(12) United States Patent
Gasper et al.

(10) Patent No.: US 9,370,594 B2
(45) Date of Patent: Jun. 21, 2016

(54) VOLATILE MATERIAL DISPENSER AND METHOD OF RETAINING ONLY COMPATIBLE REFILLS THEREBY

(75) Inventors: Thomas P. Gasper, Germantown, WI (US); Chris A. Kubicek, East Troy, WI (US); Andrew N. Niemiec, Franklin, WI (US); Robert C. Coon, Chicago, IL (US); Bjorn Gunderson, Chicago, IL (US); Erik J. Moses, Carol Stream, IL (US); Mike O'Connor, Gurnee, IL (US)

(73) Assignee: S. C. Johnson & Son, Inc., Racine, WI (US)

( * ) Notice: Subject to any disclaimer, the term of this patent is extended or adjusted under 35 U.S.C. 154(b) by 1278 days.

(21) Appl. No.: 12/837,739

(22) Filed: Jul. 16, 2010

(65) Prior Publication Data
US 2012/0012667 A1    Jan. 19, 2012

(51) Int. Cl.
*A61L 9/03* (2006.01)
*A61L 9/12* (2006.01)

(52) U.S. Cl.
CPC .............. *A61L 9/037* (2013.01); *A61L 9/127* (2013.01); *Y10T 29/49815* (2015.01)

(58) Field of Classification Search
CPC ............. A61L 9/015; A61L 9/02; A61L 9/03; A61L 9/037; A61L 9/04; A61L 9/12; A61L 9/127; Y10T 29/49; Y10T 29/49815
USPC ....................................... 239/6, 44, 51.5, 600
See application file for complete search history.

(56) References Cited

U.S. PATENT DOCUMENTS

| | | |
|---|---|---|
| 5,038,394 A | 8/1991 | Hasegawa et al. |
| 5,222,186 A | 6/1993 | Schimanski et al. |
| 6,236,807 B1 | 5/2001 | Ruffolo et al. |
| 6,278,840 B1 | 8/2001 | Basaganas Millan |
| 6,466,739 B2 | 10/2002 | Ambrosi et al. |
| 6,603,924 B2 | 8/2003 | Brown et al. |
| 6,697,571 B2 | 2/2004 | Triplett et al. |
| 6,889,003 B2 | 5/2005 | Triplett et al. |
| 7,014,818 B2 | 3/2006 | Rymer et al. |
| 7,341,698 B2 | 3/2008 | Pedrotti et al. |
| 7,357,561 B2 | 4/2008 | Hidalgo et al. |
| 7,540,432 B2 * | 6/2009 | Majerowski et al. ........ 239/51.5 |

(Continued)

FOREIGN PATENT DOCUMENTS

| | | |
|---|---|---|
| DE | 4433954 | 3/1996 |
| EP | 0451331 A1 | 10/1991 |

(Continued)

OTHER PUBLICATIONS

PCT/US2011/001253 International Search Report dated Nov. 9, 2011.

*Primary Examiner* — Christopher Kim (57) ABSTRACT

A method of retaining only compatible refills by a volatile material dispenser includes the step of providing a dispenser having a housing and at least one movable latch disposed within the housing. The method further includes the steps of providing a compatible refill that includes a container for holding a volatile material and a wick extending from the container and inserting the refill into the housing so that the refill actuates the movable latch into engagement with a structure disposed on a neck of the refill to retain the refill within the housing. The incompatible refills are incapable of actuating the movable latch, and thus, the movable latch does not retain the incompatible refills within the housing.

14 Claims, 10 Drawing Sheets

(56) References Cited

U.S. PATENT DOCUMENTS

| | | |
|---|---|---|
| 2003/0189022 A1 | 10/2003 | Fellows et al. |
| 2006/0043619 A1 | 3/2006 | Brown et al. |
| 2006/0110144 A1 | 5/2006 | Fellows et al. |
| 2006/0249593 A1 | 11/2006 | Brown et al. |
| 2008/0011874 A1 | 1/2008 | Munagavalasa et al. |
| 2008/0279731 A1 | 11/2008 | Goreham et al. |

FOREIGN PATENT DOCUMENTS

| | | |
|---|---|---|
| EP | 1175833 A1 | 1/2002 |
| ES | 278519 | 3/1984 |
| WO | 9858692 A1 | 12/1998 |
| WO | 0076292 | 12/2000 |
| WO | 0166157 A1 | 9/2001 |

\* cited by examiner

VOLATILE MATERIAL DISPENSER AND METHOD OF RETAINING ONLY COMPATIBLE REFILLS THEREBY

CROSS REFERENCE TO RELATED APPLICATIONS

Not applicable.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates generally to volatile material dispensers and, more particularly, to volatile material dispensers that are adapted to be functionally coupled with only specific volatile material refills.

2. Description of the Background of the Invention

Multiple different volatile material dispensers are commercially sold and generally include a housing and a volatile material refill that is inserted into the housing. The refill generally includes a container or bottle for holding a volatile material therein. In some dispensers, the volatile material is passively emitted therefrom. In other dispensers, a diffusion element is utilized to facilitate the dispensing of the volatile material. Examples of diffusion elements include heaters, piezoelectric elements, fans, aerosol actuators, and the like. Regardless of the mariner in which the volatile material is emitted, once the volatile material has been expended from the refill, the refill can typically be removed by a user and replaced with a new refill.

One type of commercial volatile material dispenser, referred to herein as a plug-in scented oil dispenser, includes a housing and a heater disposed within the housing. A refill for use with a plug-in scented oil dispenser generally includes a container portion having a bottom end and a top end, wherein the container portion terminates in a neck portion at the top end. A volatile material is disposed within the container portion and a wick is in contact with the volatile material and extends out of the refill through the neck portion. A plug or other connector generally positions and retains the wick within the neck portion. Upon insertion of the refill into the dispenser, at least a portion of the wick is disposed adjacent the heater such that volatile material that moves through the wick is volatilized by the heater.

Another feature of various volatile material dispensers and refills is that each refill has features that are unique or complementary to the particular dimensions of the housing of the dispenser for which it is sold. Still further, each type of dispenser is generally adapted to accept only a single type of refill having features unique or complementary to that dispenser. For example, plug-in scented oil dispensers sold by S. C. Johnson & Son, Inc. ("S. C. Johnson") of Racine, Wis., generally only accept refills sold by S. C. Johnson under their Glade® brand and such refills are designed to fit only within S. C. Johnson plug-in scented oil dispensers. Similarly, plug-in scented oil dispensers sold by Reckitt Benckiser ("Reckitt") of Berkshire, England generally only accept refills sold by Reckitt under their Air Wick® brand and such refills are designed to generally fit only within Reckitt plug-in scented oil dispensers. Still similarly, plug-in scented oil dispensers sold by Procter & Gamble ("P&G") of Cincinnati, Ohio and such refills are designed to fit only with P&G plug-in scented oil dispensers. This is generally the case for most commercial plug-in scented oil dispensers and refills therefor.

SUMMARY OF THE INVENTION

According to one embodiment, a method of retaining only compatible refills by a volatile material dispenser includes the step of providing a dispenser having a housing and at least one movable latch disposed within the housing. The method further includes the steps of providing a compatible refill that includes a container for holding a volatile material and a wick extending from the container and inserting the refill into the housing so that the refill actuates the movable latch into engagement with a structure disposed on a neck of the refill to retain the refill within the housing. The incompatible refills are incapable of actuating the movable latch, and thus, the movable latch does not retain the incompatible refills within the housing.

According to another embodiment, a volatile material dispenser includes a housing forming a cavity for disposal of a refill having a volatile material therein and a wick in contact with the volatile material and extending out of the refill. The dispenser further includes a movable latch disposed within the housing, wherein the latch includes a lever connected to a first end of a movable arm at a pivot point and a latch member is disposed at a second end of the movable arm to aid in securing the refill within the dispenser.

According to yet another embodiment, a method of retaining only compatible refills by a volatile material dispenser includes the steps of providing a dispenser having a housing and providing a compatible refill that includes a container for holding a volatile material, a neck portion extending from the container, and a wick in contact with the volatile material and extending out the container, wherein the neck portion has a first set of dimensions. The method further includes the step of providing a movable latch in the housing, wherein the movable latch is actuated when the compatible refill is inserted into the housing to retain the compatible refill within the housing. The movable latch is not actuated when an incompatible refill having a container for holding a volatile material, a neck portion extending from the container and having a second set of dimensions different from the first set of dimensions, and a wick in contact with the volatile material and extending out of the container is inserted into the housing, thereby preventing retention of the incompatible refill in the housing.

Other aspects and advantages of the present invention will become apparent upon consideration of the following detailed description.

BRIEF DESCRIPTION OF THE DRAWINGS

Other aspects and advantages of the present invention will become apparent upon consideration of the following detailed description, wherein similar structures have like or similar reference numerals.

DETAILED DESCRIPTION

The present invention is directed to volatile material dispensers for vaporizing and dispensing volatile materials. While the present invention may be embodied in many different forms, several specific embodiments are discussed herein with the understanding that the present invention is to be considered only as an exemplification of the principles of the invention, and it is not intended to limit the invention to the embodiments illustrated.

Further, the use of the term volatile material herein refers to any volatile material that a consumer may desire to emit into an area surrounding one or more refills holding the volatile material(s) and/or a dispenser holding one or more refills. Illustratively, the types of volatile materials may be, for example, a cleaner, an insecticide, an insect repellant, an insect attractant, a mold or mildew inhibitor, a fragrance, a disinfectant, an air purifier, an aromatherapy scent, an antiseptic, a positive fragrancing volatile material, an air-freshener, a deodorizer, or the like, and combinations thereof. Additives may be included in the volatile material, such as, for example, fragrances and/or preservatives.

Figure 1:
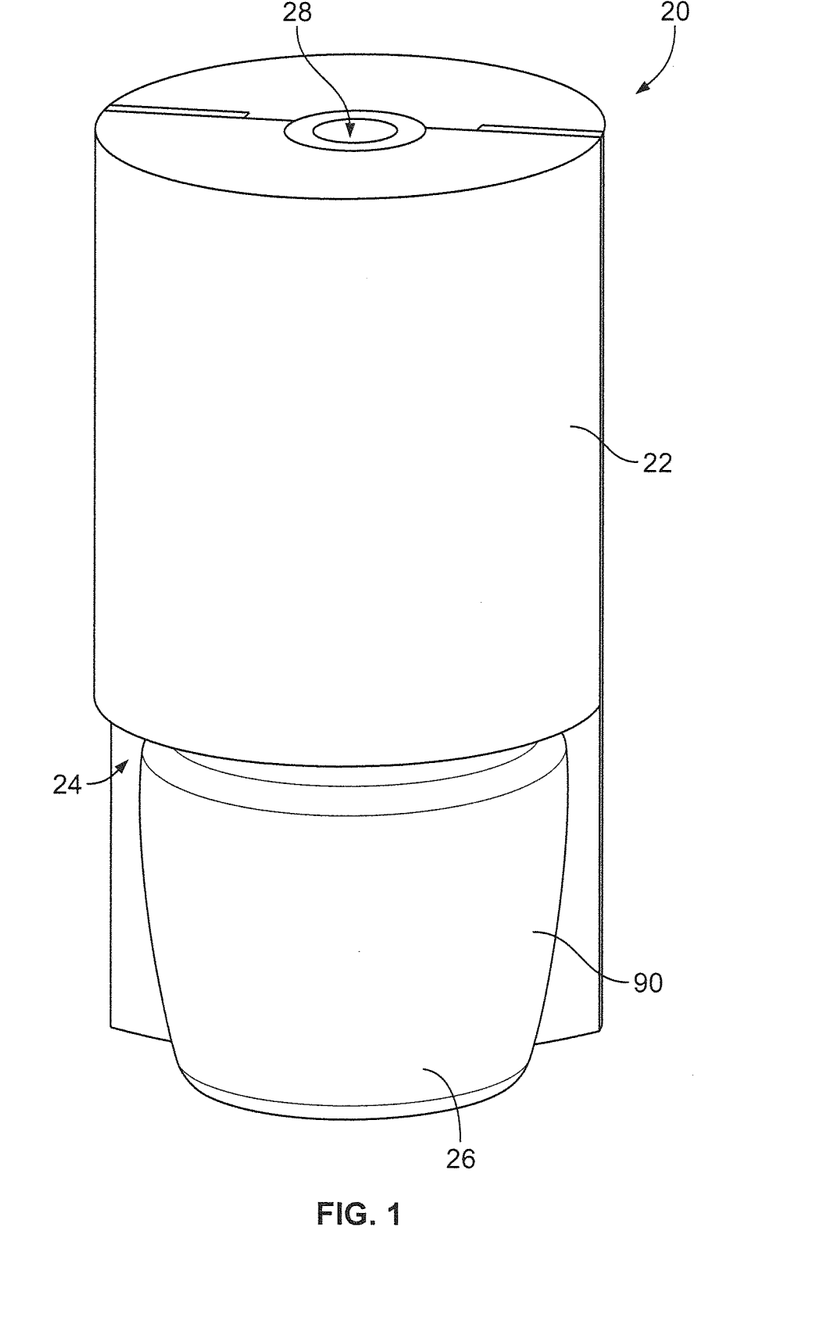
FIG. 1 is a top isometric view of a volatile material dispenser with a compatible refill retained therein.

Referring now to FIG. 1, a volatile material dispenser 20 includes a housing 22 having a cavity 24 for accepting a compatible volatile material refill 26 and an optional diffusion element or elements (not shown) disposed in the housing 22. The diffusion element may be a heater, a fan, a piezoelectric element, or any other diffusion element or combination of diffusion elements known in the art. The housing 22 further includes a channel 28 (FIGS. 1-6) for receiving a wick disposed within the refill 26 and a retention mechanism 30 for attaching the refill 26 to the housing 22. The dispenser 20 may include any number of electrical or mechanical features that aid in vaporizing and/or dispensing the volatile material, provide aesthetics for the dispenser 20, and/or provide other functional features to the dispenser 20, as long as appropriate features are present in the dispenser 20 to retain the refill 26 therein.

Figure 2:
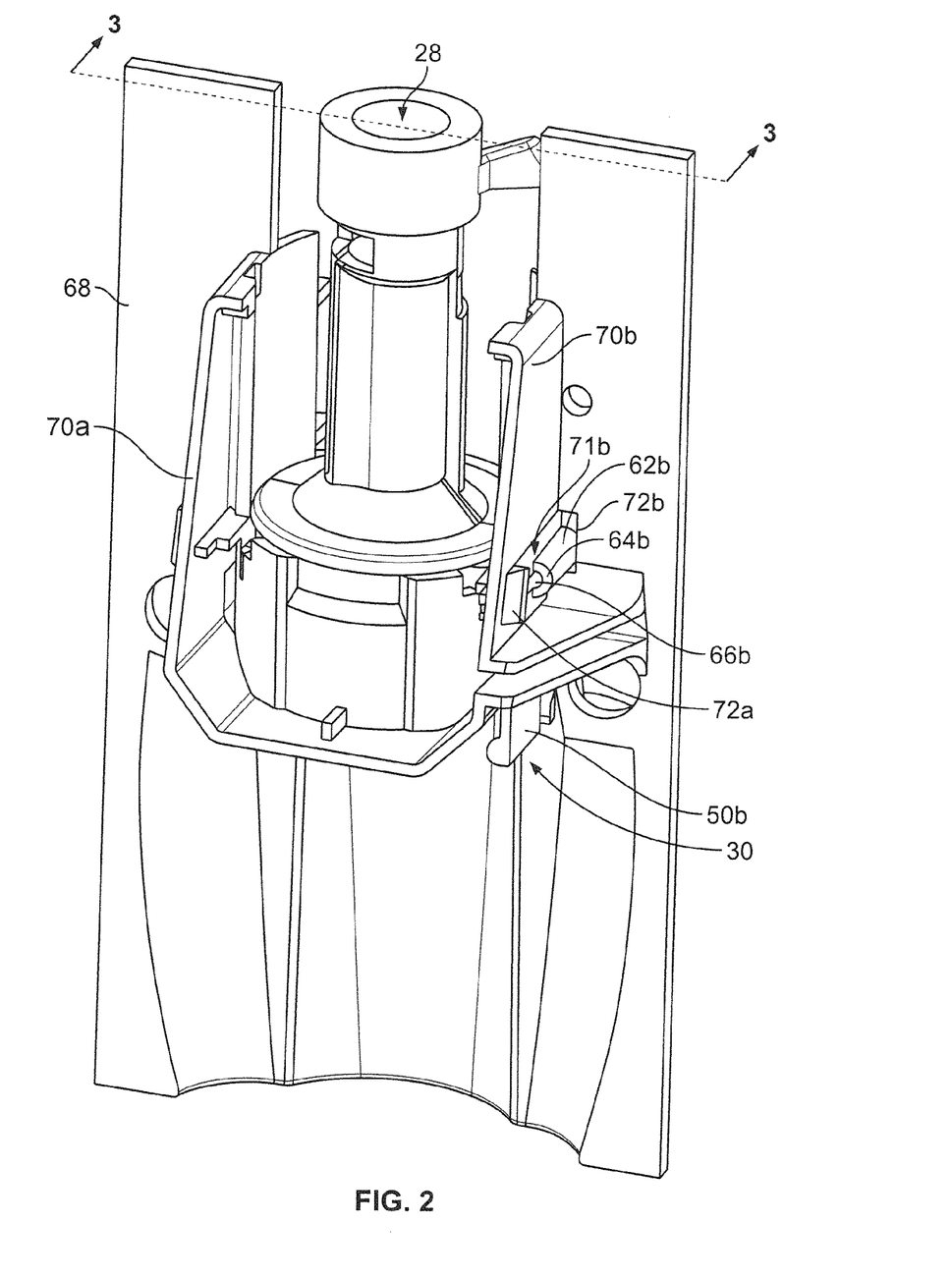
FIG. 2 is a top isometric view of the volatile material dispenser of FIG. 1 employing a first embodiment of a retention mechanism, wherein a housing and the compatible refill are removed therefrom.
Figure 3:
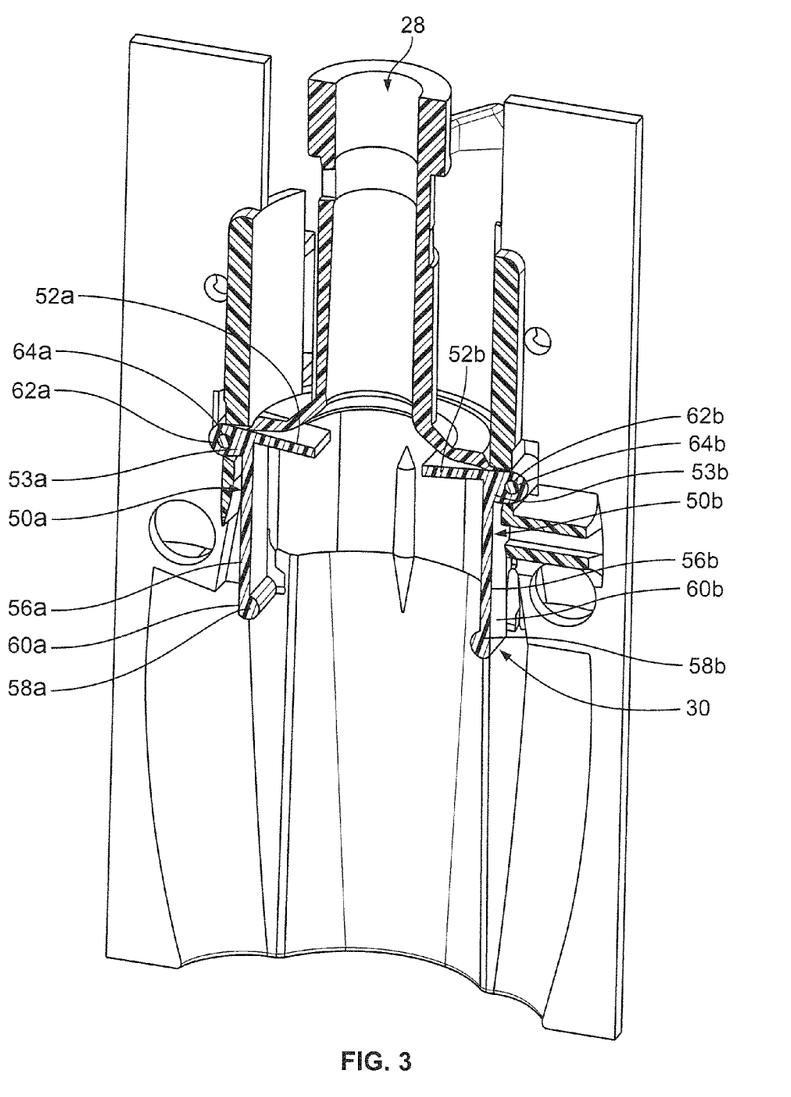
FIG. 3 is a cross-sectional view taken generally along the lines 3-3 of FIG. 2.
Figure 4:
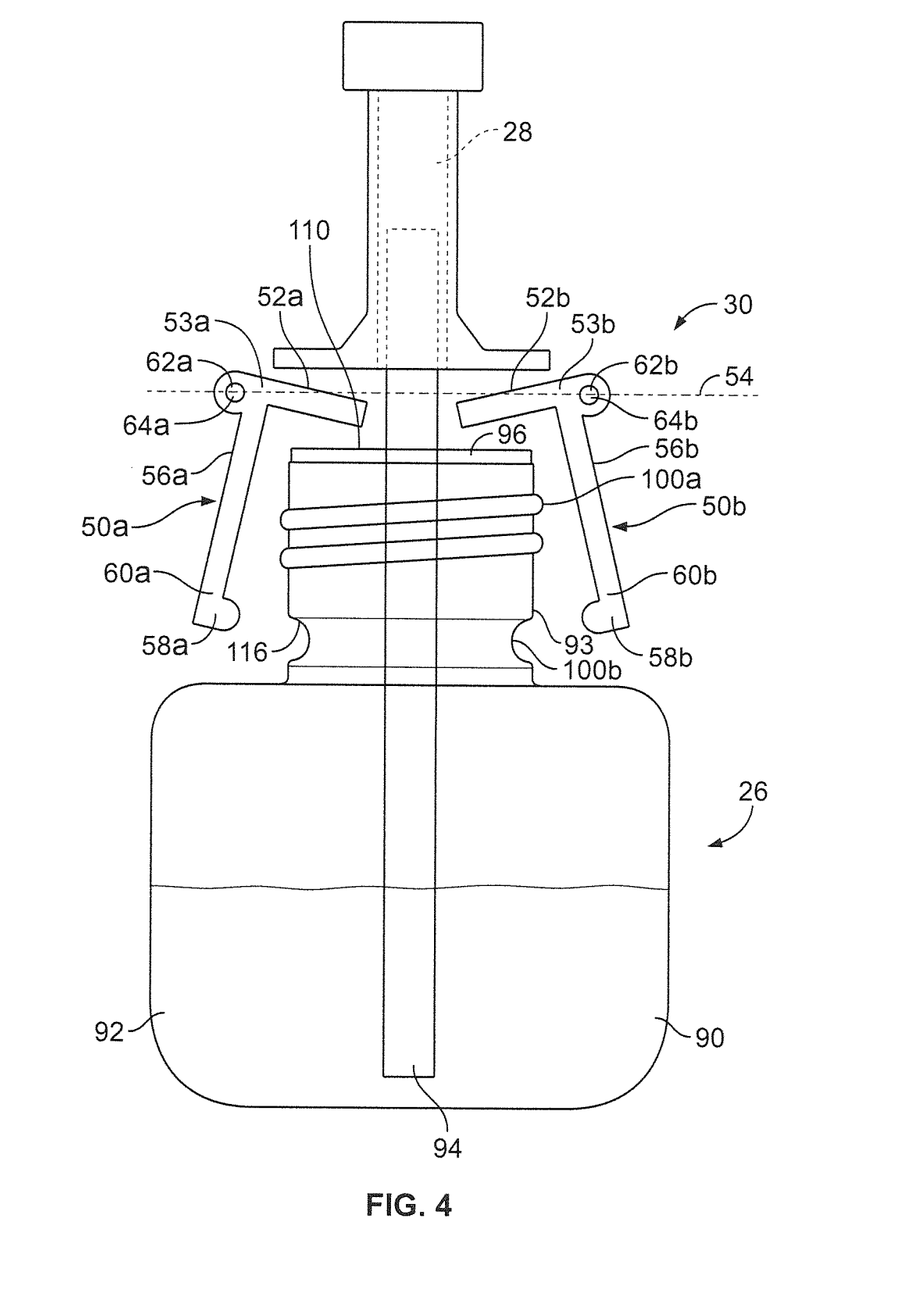
FIG. 4 is a front elevational view of the retention mechanism of FIG. 2 depicting the compatible refill being inserted therein.
Figure 5:
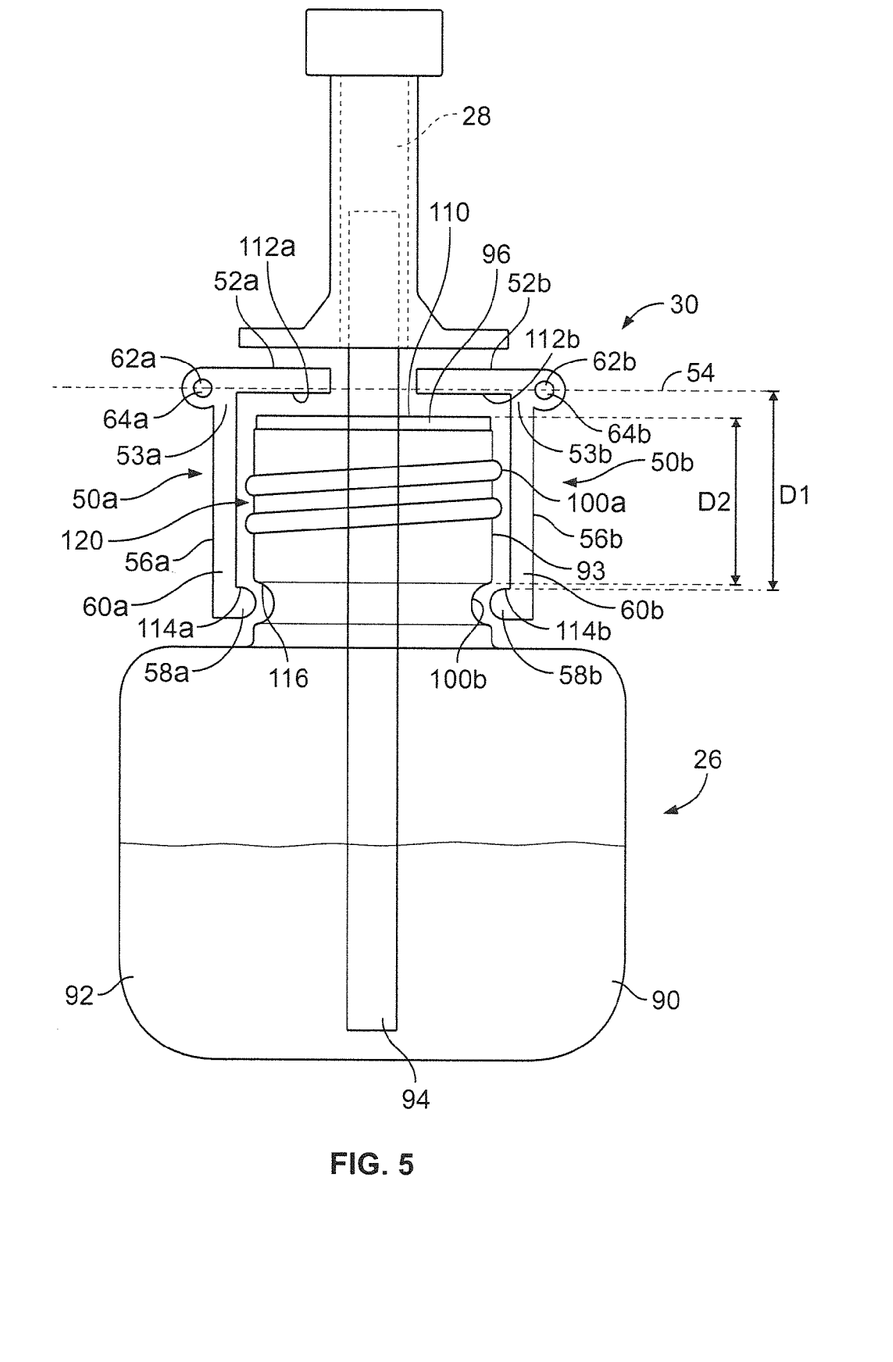
FIG. 5 is a front elevational view of the retention mechanism of FIG. 2 depicting the compatible refill retained therein.

A first embodiment of a retention mechanism 30, as seen in FIGS. 2-6, in the form of movable latches 50a, 50b is disposed within the housing 22 to retain compatible refills 26 therein, but prevent retention of incompatible refills. Each of the movable latches 50a, 50b includes a lever 52a, 52b at an upper end 53a, 53b thereof, wherein the levers 52a, 52b are disposed at an angle with respect to a horizontal axis 54 when no refill 26 is installed therein, as seen in FIG. 4, and are generally aligned with the axis 54 when a refill 26 is installed therein, as seen in FIG. 5. The latches 50a, 50b further include arms 56a, 56b extending at about a 90 degree angle from respective levers 52a, 52b and having latch members 58a, 58b at lower ends 60a, 60b of the arms 56a, 56b. The latch members 58a, 58b, although depicted as having bulbous projections extending inwardly therefrom, may include any other feature in any shape, size, or number that would allow the latches 50a, 50b to grasp and retain a refill 26. In particular, the latch members 58a, 58b may include grooves, triangular projections, notches, hook and loop fasteners, adhesive, ribs, or any other known fastener. Each of the levers 52a, 52b is connected to a respective arm 56a, 56b by a pivot point 62a, 62b. In one embodiment, the pivot points 62a, 62b are formed by apertures 64a, 64b extending through the latches 56a, 56b between the respective levers 52a, 52b and arms 56a, 56b and pins or posts 66a, 66b (only 66b is shown; FIG. 2) disposed through respective apertures 64a, 64b and connected to the housing 22. As one skilled in the art would appreciate, any other mechanism known in the art to allow pivoting may be utilized. Although two latches 50a, 50b are depicted, one or more latches may be utilized, as long as the number of latches allows retention of the refill 26 within the dispenser 20.

Referring to FIG. 2, the pins 66a, 66b are formed as part of the housing 22. In particular, the housing 22 includes a generally vertical chassis 68 to which a number of internal components are connected. A set of walls 70a, 70b extend outwardly from the chassis 68 and surround the channel 28 that houses a wick when a refill is inserted therein. As only the features related to the latch 50b are visible in FIG. 2, the connection of only such latch 50b will be described, it being understood that the connection of the latch 50a is identical.

The wall 70b includes an aperture 71b therethrough through which the pivot point 62b of the latch 50b extends. End walls 72a, 72b extend generally perpendicularly from the wall 70b. The pin 66b is connected to and extends between the end walls 72a, 72b with the pin 66b extending through the aperture 64b to support the latch 50b.

Although one method of attaching the latches 50a, 50b to the housing is described, it would be understood by one skilled in the art that the latches 50a, 50b may be rotationally or pivotally affixed to the housing 22 in any number of manners.

FIGS. 4 and 5 depict the retention mechanism 30 in the form of movable latches 50a, 50b and a compatible refill 26, which includes a bottle or container 90 with a volatile material 92 disposed therein and a generally cylindrical neck portion 93 extending outwardly from the container 90. The volatile material 92 disposed in the container 90 may be any type of volatile material adapted to be dispensed into the ar. An elongate wick 94 is in contact with the volatile material 92 in the container 90 and extends out of the container 90 through the neck portion 93 so that at least a portion of the wick 94 is exposed to the ambient environment. A plug assembly 96 holds the wick 94 in place with respect to the container 90. The wick 94 is depicted as a substantially uniform cylinder with a substantially constant diameter throughout an entire length thereof. However, in other embodiments, the wick 94 may be other shapes and sizes as known in the art. The wick 94 may be made of one material or alternatively may be made of multiple materials, e.g., polymeric or porous materials and/or any other material known in the art that are suitable for wicking.

The compatible refill 26 includes at least one retention structure thereon. As shown in FIGS. 4 and 5, the depicted compatible refill 26 includes a first optional retention structure 100a in the form of threading formed on the neck portion 93 of the refill 26. The threading 100a is intended to cooperate with threaded grooves on a cap (not shown) to attach and retain a cap on the refill 26 during shipment and storage of the refill 26. A second retention structure 100b in the form of an annular groove is disposed below the threading 100a and provides an interference for the latch members 58a, 58b in the movable latches 50a, 50b to aid in retaining the refill 26 within the dispenser 20, as will be discussed in detail hereinafter. Although the groove 100b is shown as annular, the groove 100b may optionally be discontinuous or formed of only one or two opposing grooves. Still optionally, in other embodiments, any structure that cooperates with the latch members 58a, 58b may be utilized, such as, for example, an annular projection, triangular or circular projections, notches, hook and loop fasteners, adhesive, ribs, or any other known fastener.

Referring to FIG. 5, the compatible refill 26 is shown retained within the movable latches 50a, 50b. Before insertion of the refill 26 (FIG. 4), the arms 56a, 56b and latch members 58a, 58b are rotated outwardly and the levers 52a, 52b are rotated downwardly. As the refill 26 is inserted into the dispenser 20, a top surface 110 of the neck portion 93 of the refill 26 reaches the levers 52a, 52b and begins to push the levers 52a, 52b upwardly, thereby rotating the latches 50a, 50b about the pivot points 62a, 62b. As the latches 50a, 50b rotate, the latch members 58a, 58b rotate inwardly until the levers 52a, 52b are generally aligned with the axis 54 (generally horizontal) and the arms 56a, 56b are generally perpendicular to the axis 54 (generally vertical). In this position, the latch members 58a, 58b interfere with the retention structure 100b on the neck portion 93 of the refill 26 to prevent movement of the refill 26 out of the dispenser 20. Further, a size of the neck portion 93 and a placement of the retention structure 100b prevent outward rotation of the latches 50a, 50b. In particular and referring to FIG. 5, a distance D1 between lower surfaces 112a, 112b of the levers 52a, 52b and upper surfaces 114a, 114b of latch members 58a, 58b is only slightly greater than a distance D2 between the top surface 110 of the neck portion 93 and a retention surface 116 of the retention structure 100b. In particular, the distance D2 is preferably between about 75% and about 100% of the distance D1, and more preferably about 90% of the distance D1. The distance D2 must be great enough that, when the latch members 58a, 58b grasp the retention structure 100b, the top surface 110 of the neck portion 93 retains the levers 52a, 52b in alignment with the axis 54. The levers 52a, 52b, arms 56a, 56b, and latch members 58a, 58b create a cavity 120 that retains the neck portion 93 of the refill, but that will not retain an incompatible refill that has a differently sized or shaped neck portion.

Figure 6:
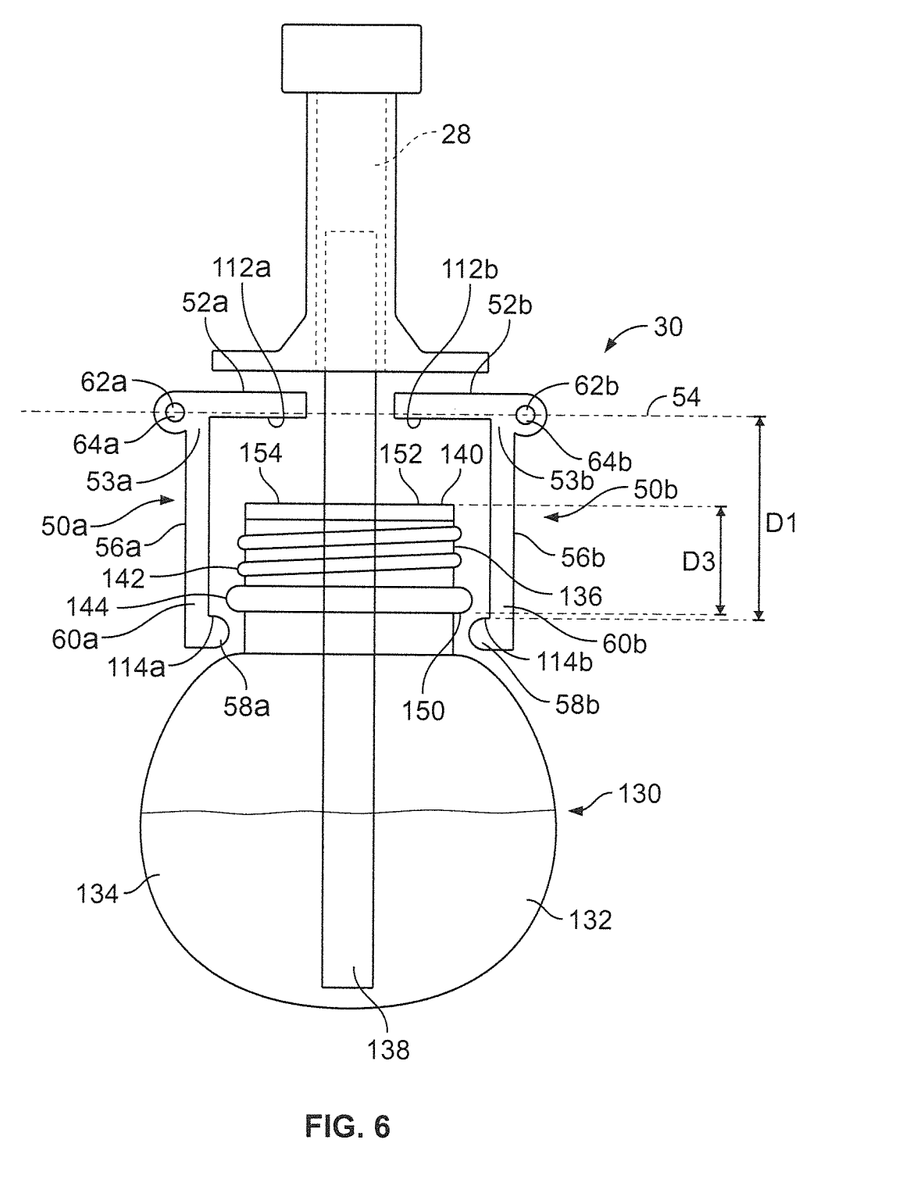
FIG. 6 is a front elevational view of the retention mechanism of FIG. 2 depicting an attempt at inserting an incompatible refill therein.

Referring to FIG. 6, an incompatible refill 130 is shown being inserted into the dispenser 20. The incompatible refill 130 has some features similar to the compatible refill 26. In particular, the incompatible refill 130 includes a bottle or container 132 with a volatile material 134 disposed therein and a generally cylindrical neck portion 136 extending outwardly from the container 132. A wick 138 is in contact with the volatile material 134 in the container 132 and extends out of the container 132 through the neck portion 136. A plug assembly 140 holds the wick 138 with respect to the container 132. The neck portion 136 has a thread 142 extending therefrom for holding a cap (not shown) thereon and/or retaining the refill 26 within a dispenser. The neck portion 136 may also include a retaining structure 144, such as one or more annular rings, ridges, or other projections, that interact with retention mechanisms within a dispenser.

The incompatible refill 130 is incompatible in a sense that it cannot be retained by the movable latches 50a, 50b because it has features that are not compatible therewith. For example, a size and/or shape of the neck portion 136 may not be sized properly to fit within the latches 50a, 50b, the neck portion 136 may not have the proper feature(s) or feature(s) in the proper position to retain the refill 26, etc. A distance D3 defines a distance between a lowermost end 150 of any retention structure on the neck portion 136 of the incompatible refill 130 (here, retention structure 144) and an uppermost end 152 of the neck portion 136. The distance D3 is less than about 74% of the distance D1. The distance D3 is small enough that, when a top surface 154 of the neck portion 136 reaches the levers 52a, 52b (if the top surface 154 can even reach the levers 52a, 52b), the latch members 58a, 58b are spaced so far away from the retaining structure 144 or any structure on the neck portion 136 (due to a short neck portion 136), that the latch members 58a, 58b are unable to retain the refill 26. If the refill 26 is moved downwardly such that the latch members 58a, 5 8b are in contact with the retaining structure 144, the top surface 154 of the neck portion 136 is too far away from the levers 52a, 52b to retain same in a generally horizontal position aligned with the axis 54, and therefore, the latches 50a, 50b rotate outwardly and prevent attachment of the refill 26.

A second embodiment of a retention mechanism 30 disposed within the dispenser 20 is depicted in FIGS. 7-11. The retention mechanism 30 is in the form of a movable latch 300 disposed within the housing 22 to retain compatible refills 26 therein, but prevent retention of incompatible refills. The movable latch 300 includes a ring-shaped lever 302 having an aperture 304 therethrough that is aligned with the channel 28 in the housing 22 for insertion of a wick therethrough. Two arms 306a, 306b extend outwardly and downwardly from the ring-shaped lever 302 and are connected to the lever 302 at first ends 308a, 308b of the arms 306a, 306b by living hinges 310a, 310b, wherein each of the arms 306a, 306b includes a latch member 312a, 312b disposed at an end 314a, 314b thereof. The latch members 312a, 312b may be any structure as detailed above with respect to the first embodiment of FIGS. 2-6. Although living hinges 310a, 310b are utilized in this embodiment, any other pivoting or rotating mechanism may be utilized, as one skilled in the art would appreciate. Further, although two arms 306a, 306b are employed, one or more arms may be employed as long as the refill 26 can be retained thereby within the dispenser 20.

Figure 7:
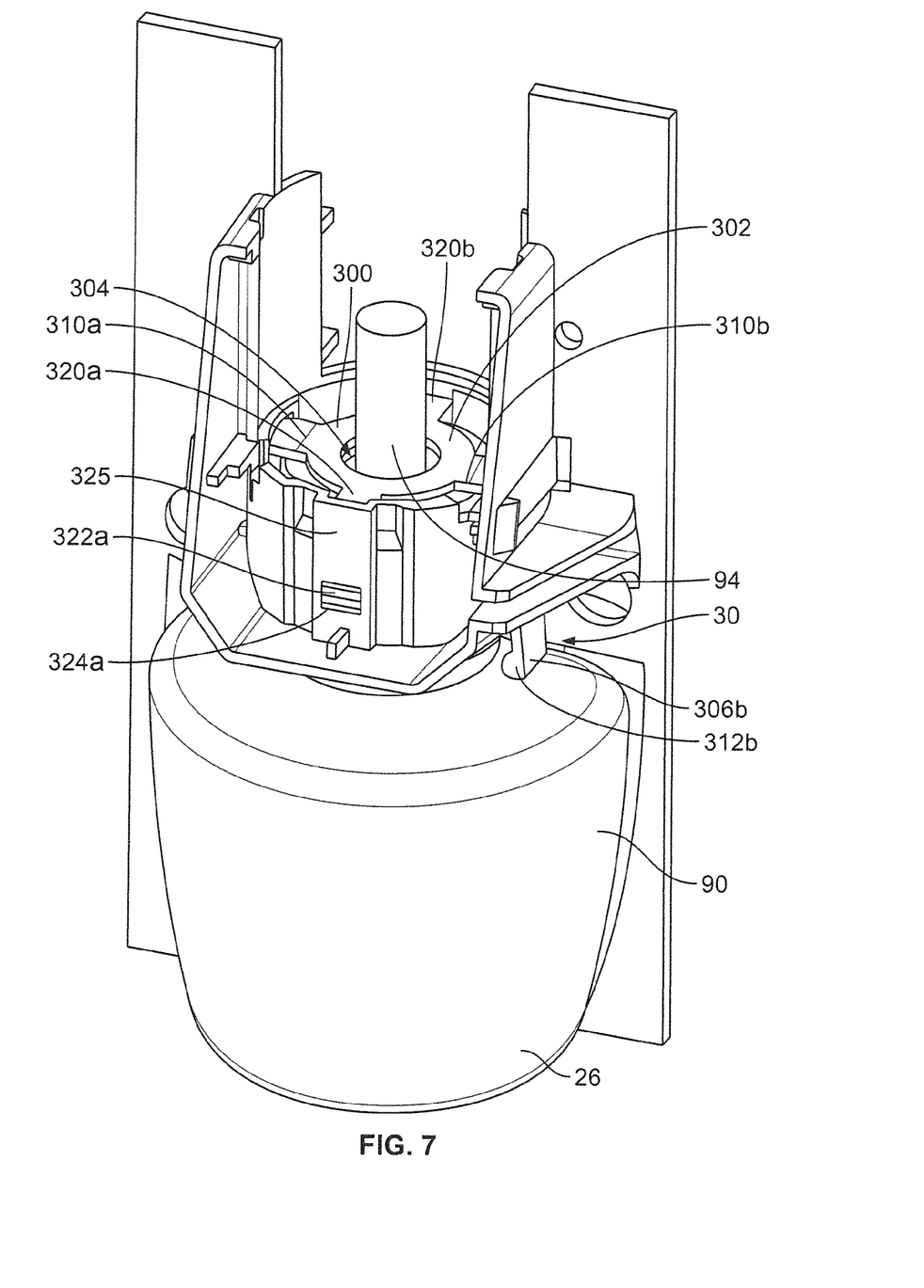
FIG. 7 is a top isometric view of the volatile material dispenser of FIG. 1 employing a second embodiment of a retention mechanism, wherein portions of the housing are removed therefrom.
Figure 8:
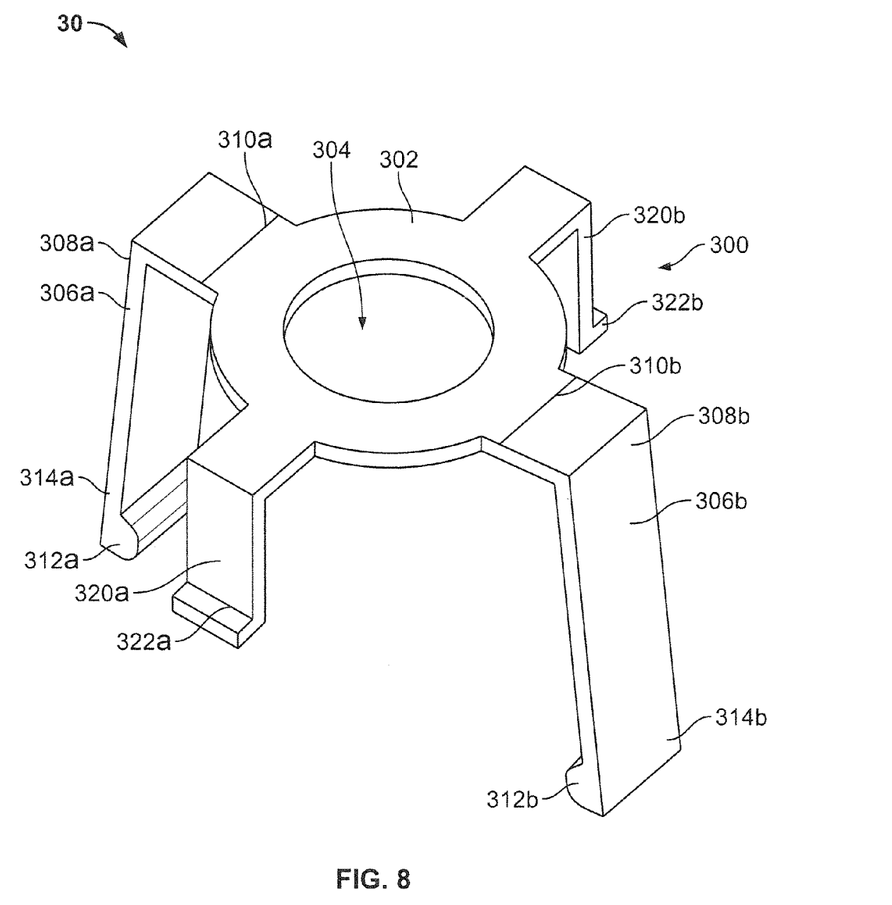
FIG. 8 is a top isometric view of the retention mechanism of FIG. 7.

As seen in FIGS. 7 and 8, the latch 300 is attached to the housing by first and second L-shaped legs 320a, 320b disposed 180 degrees from one another and 90 degrees from each of the arms 306a, 306b. Each of the legs 320a, 320b includes a clip or other projection 322a, 322b that extends into apertures 324a, 324b (only 324a shown; FIG. 7) formed within walls 325 in the housing 22 of the dispenser 20 to locate and retain the latch 300. The legs 320a, 320b are biased outwardly such that, when the legs 320a, 320b are pressed inwardly to pass the walls 325, the legs 320a, 320b snap outwardly when the clips 322a, 322b reach the apertures 324a, 324b. Optionally, any other mechanism known in the art may be utilized, such as, for example, a bayonet-type mounting, grooves, notches, projections, hook and loop fasteners, adhesive, ribs, or any other known attachment mechanism.

Figure 9:
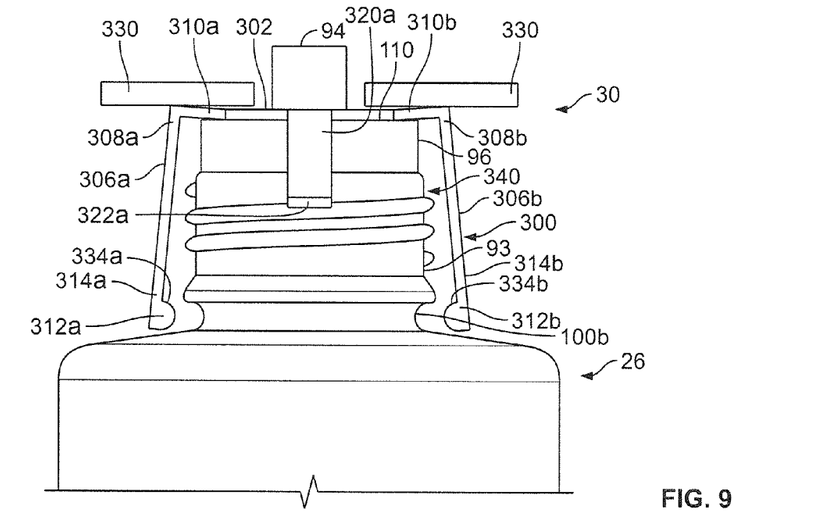
FIG. 9 is a front elevational view of the retention mechanism of FIG. 7 depicting the compatible refill being inserted therein.
Figure 10:
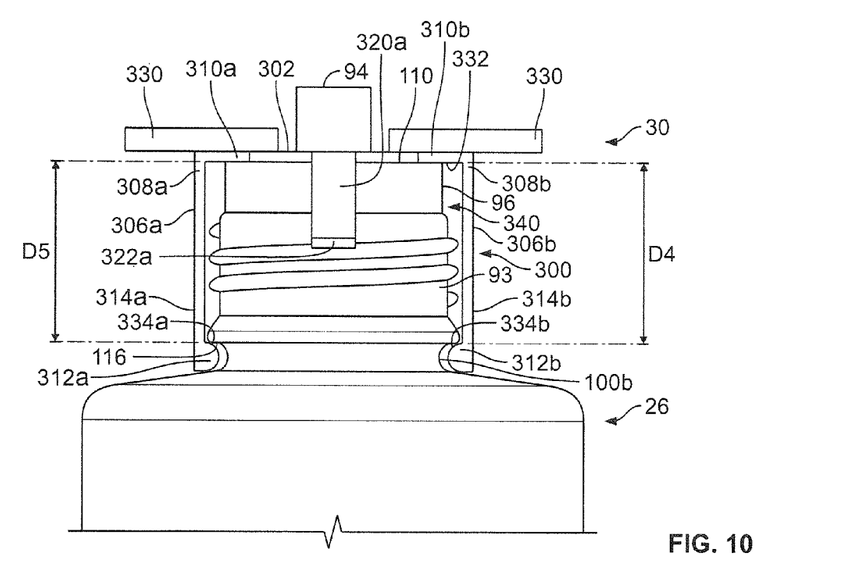
FIG. 10 is a front elevational view of the retention mechanism of FIG. 7 depicting the compatible refill retained therein.
Figure 11:
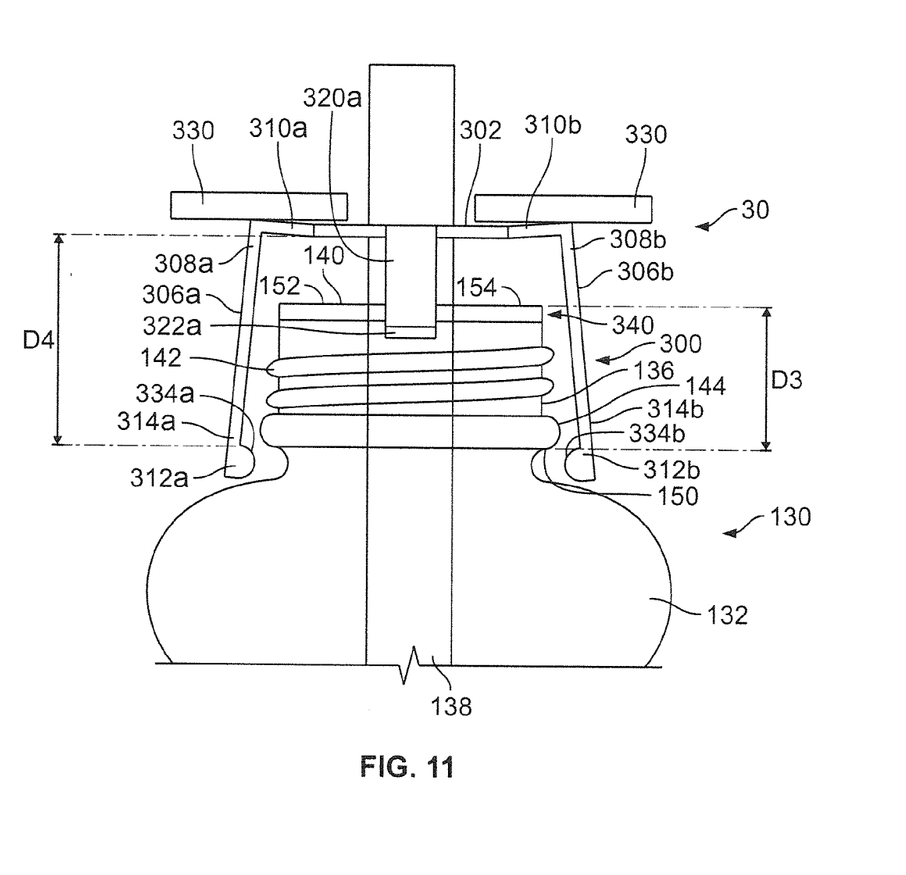
FIG. 11 a front elevational view of the retention mechanism of FIG. 7 depicting an attempt at inserting an incompatible refill therein.

Attachment of the compatible refill 26 to the dispenser 20 having the movable latch 300 of FIGS. 7 and 8 is depicted in FIGS. 9 and 10 and is similar to the attachment as described above with respect to FIGS. 4 and 5. In particular, before insertion of the refill 26, the arms 306a, 306b and latch members 312a, 312b are rotated outwardly and an inactivation of the living hinges 310a, 310b causes the ring-shaped lever 302 to be in a lower position, as seen in FIG. 9. As the refill 26 is inserted into the dispenser 20, the top surface 110 of the neck portion 93 of the refill 26 reaches the ring-shaped lever 302 and begins to push the lever 302 upwardly into a highest position, as seen in FIG. 10, until the lever 302 reaches a surface 330 parallel thereto, thereby activating the living hinges 310a, 310b and causing the arms 306a, 306b and latch members 312a, 312b to rotate inwardly to a generally vertical position (perpendicular to the lever 302). In this position, the latch members 312a, 312b interfere with the retention structure 100b on the neck portion 93 of the refill 26 to prevent movement of the refill 26 out of the dispenser 20. As with the embodiment of FIGS. 2-6, a size of the neck portion 93 and a placement of the retention structure 100b on the refill 26 prevent outward rotation of the arms 306a, 306b. In particular, as seen in FIG. 10, a distance D4 between a lower surface 332 of the lever 302 and upper surfaces 334a, 334b of the latch members 312a, 312b is only slightly greater than a distance D5 between the top surface 110 of the neck portion 93 and a retention surface 116 of the retention structure 100b. As with D1 and D2, the distance D5 is preferably between about 75% and about 100% of the distance D4, and more preferably about 90% of the distance D4. The distance D5 must be great enough that, when the latch members 312a, 312 grasp the retention structure 100b, the top surface 110 of the neck portion 93 retains the lever 302 in the highest position of FIG. 10. The lever 302, arms 306a, 306b, and latch members 312a, 312b create a cavity 340 that retains the neck portion 93 of the refill 26, but that will not retain an incompatible refill, as described in detail below.

As with the embodiment of FIGS. 2-6, the incompatible refill 130 cannot be retained within the dispenser 20 by the movable latch 300 because it has features that are not compatible therewith. The distance D3, defined above, is less than about 74% of the distance D4. The distance D3 is small enough that, when the top surface 154 of the neck portion 136 reaches the lever 302 (if this is even possible), the latch members 312a, 312b are spaced so far away from the retaining structure 144 or any other structure on the neck portion 136 (due to a short neck portion 136) that the latch members 312a, 312b are unable to retain the refill 130. If the refill 130 is moved downwardly such that the latch members 312a, 312b are aligned with the retaining structure 144, the top surface 154 of the neck portion 136 is too far away from the lever 302 to retain same in its highest position, and therefore, the arms 306a, 306b rotate outwardly and prevent attachment of the refill 130.

Although directional language, such as horizontal, upper, lower, etc., is used herein, such terminology is meant to describe the relation of components herein and not to limit the scope of the present invention. In particular, such directional language is utilized in the case that the dispenser 20 is disposed in a use position and, as one skilled in the art would recognize, the dispenser 20 may be reoriented, but the same relative nature of the components applies.

Any of the embodiments described herein may be modified to include any of the structures or methodologies disclosed in connection with other embodiments.

INDUSTRIAL APPLICABILITY

The present invention provides a volatile material dispenser that is adapted for use with only compatible volatile material refills. In particular, a rotatable retaining mechanism is disposed within the dispenser and actuated by only compatible refills to retain the compatible refills within the dispenser. Incompatible refills do not actuate the mechanism, and thus the mechanism does not retain the incompatible refills therein.

Numerous modifications to the present invention will be apparent to those skilled in the art in view of the foregoing description. Accordingly, this description is to be construed as illustrative only and is presented to enable those skilled in the art to make and use the invention and to teach the best mode of carrying out same. The exclusive rights to all modifications that come within the scope of the appended claims are reserved.

We claim:

1. A method of retaining only compatible refills by a volatile material dispenser, the method comprising the steps of:
   providing a dispenser having a housing and at least one rotatable latch disposed within the housing;
   providing a compatible refill that includes a container for holding a volatile material and a wick extending from the container; and
   inserting the refill into the housing so that the refill rotates the rotatable latch into engagement with a structure disposed on a neck of the refill to retain the refill within the housing;
   wherein during the inserting step, a top surface of a neck portion of the refill is the first portion of the refill to contact the movable latch, thereby rotating the latch into engagement with the structure disposed on the neck of the refill;
   wherein incompatible refills are incapable of actuating the rotatable latch, and thus, the rotatable latch does not retain the incompatible refills within the housing.

2. The method of claim 1 further including the step of providing the rotatable latch with a lever at an upper end thereof and an arm extending at about 90 degrees from the lever and having a latch member at a lower end thereof.

3. The method of claim 2 further including the step of connecting the lever and the arm at a pivot point, wherein the latch is rotatable about the pivot point.

4. The method of claim 3, wherein the pivot point is formed by a pin disposed through an aperture in the latch and the pin is connected to the housing to allow rotation of the latch about the pivot point.

5. The method of claim 4, wherein the inserting step includes sizing the neck of the compatible refill such that, a first distance between an uppermost surface of the compatible refill and a retention surface on the compatible refill is between about 75% and about 100% of a second distance between a lower surface of the lever and an upper surface of the latch member.

6. The method of claim 5, wherein a third distance between a lowermost end of a retention structure on an incompatible refill and an uppermost end of a neck portion on the incompatible refill is less than about 74% of the second distance.

7. The method of claim 1 further including the step of providing the movable latch with a ring-shaped lever for insertion of the wick therethrough and at least one arm extending from the ring-shaped member and having a latch member at an end thereof.

8. The method of claim 7 further including the step of providing a living hinge between the ring-shaped lever and the at least one arm to allow the at least one arm to rotate about the living hinge.

9. The method of claim 8, wherein the inserting step includes sizing the neck of the compatible refill such that, a first distance between an uppermost surface of the compatible refill and a retention surface on the compatible refill is between about 75% and about 100% of a second distance between a lower surface of the lever and an upper surface of the latch member.

10. The method of claim 9, wherein a third distance between a lowermost end of a retention structure on an incompatible refill and an uppermost end of a neck portion on the incompatible refill is less than about 74% of the second distance.

11. A method of retaining only compatible refills by a volatile material dispenser, the method comprising the steps of:
providing a dispenser having a housing;
providing a compatible refill that includes a container for holding a volatile material, a neck portion extending from the container, and a wick in contact with the volatile material and extending out the container, wherein the neck portion has a first set of dimensions;
providing a movable latch in the housing, wherein the movable latch is actuated when the compatible refill is inserted into the housing to retain the compatible refill within the housing and the movable latch is not actuated when an incompatible refill having a container for holding a volatile material, a neck portion extending from the container and having a second set of dimensions different from the first set of dimensions, and a wick in contact with the volatile material and extending out of the container is inserted into the housing, thereby preventing retention of the incompatible refill in the housing;
wherein a top surface of the neck portion of the compatible refill contacts the movable latch to actuate the movable latch to retain the compatible refill.

12. The method of claim 11 further including the steps of providing the movable latch with a lever at an upper end thereof and an arm extending at about 90 degrees from the lever and having a latch member at a lower end thereof and connecting the lever and the arm at a pivot point such that the latch is rotatable about the pivot point.

13. The method of claim 11 further including the steps of providing the movable latch with a ring-shaped lever for insertion of the wick therethrough and at least one arm extending from the ring-shaped member and having a latch member at an end thereof and providing a living hinge between the ring-shaped lever and the at least one arm to allow the at least one arm to rotate at the living hinge.

14. The method of claim 12, wherein a first distance between the an uppermost surface of the compatible refill and a retention surface on the compatible refill is between about 75% and about 100% of a second distance between a lower surface of the lever and an upper surface of the latch member.

* * * * *